United States Patent [19]

Brier

[11] Patent Number: 4,664,663
[45] Date of Patent: May 12, 1987

[54] DISPOSABLE WATERPROOF ENCASEMENT AND PANTY FOR SANITARY PAD

[75] Inventor: Michael I. Brier, Philadelphia, Pa.

[73] Assignee: Hygienics Industries, Inc., Philadelphia, Pa.

[21] Appl. No.: 698,355

[22] Filed: Feb. 5, 1985

Related U.S. Application Data

[63] Continuation-in-part of Ser. No. 579,340, Feb. 13, 1984, abandoned.

[51] Int. Cl.$^4$ .................................................. A61F 13/16
[52] U.S. Cl. ................................... 604/387; 604/397
[58] Field of Search ............................... 604/385–387, 604/389, 393, 395, 397, 398

[56] References Cited

U.S. PATENT DOCUMENTS

| | | | |
|---|---|---|---|
| 791,354 | 5/1905 | Merkley | 64/400 |
| 2,295,016 | 9/1942 | Scribner | 604/387 |
| 2,551,691 | 2/1949 | Newman | 604/397 |
| 2,571,357 | 10/1951 | Gemora | 604/397 |
| 3,079,922 | 8/1961 | Papajohn | 604/397 |
| 3,880,747 | 4/1975 | Mills et al. | 208/18 |
| 4,044,769 | 8/1977 | Papajohn | 604/397 |

Primary Examiner—John D. Yasko
Attorney, Agent, or Firm—Seidel, Gonda, Goldhammer & Abbott

[57] ABSTRACT

A disposable waterproof encasement for an absorbent sanitary pad may be releasably secured to an undergarment to convert an everyday undergarment into a sanitary panty or stress incontinence garment. Preferably, the encasement is secured to the panty with the Velcro-type fasteners. The encasement includes a waterproof back and a waterproof marginal front portion secured to the marginal portion of the back to form a watertight fold. The marginal front portion forms an opening to expose the absorbent pad. The encasement may include an elongated strap bridging the central portion of the opening for retaining the absorbent pad within the encasement. One end portion of the strap may be releasably secured to the front marginal portion to facilitate insertion and removal of the absorbent pad. To ease removing the absorbent pad, the encasement may include an elasticized rubber pad.

8 Claims, 14 Drawing Figures

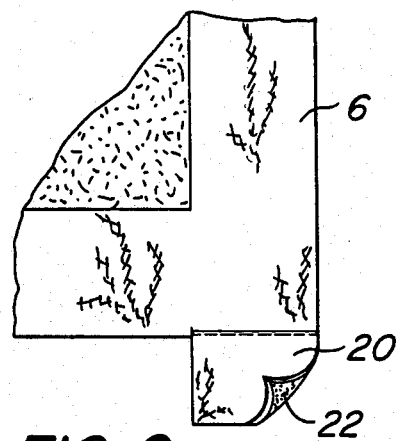
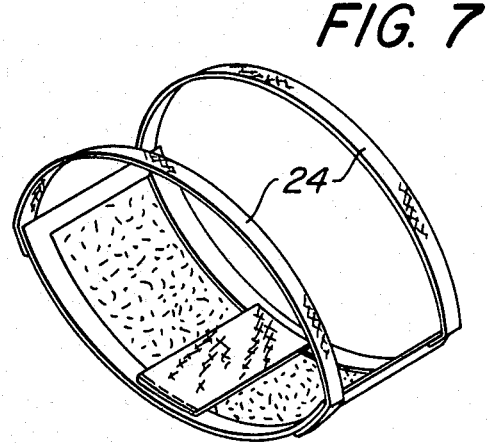
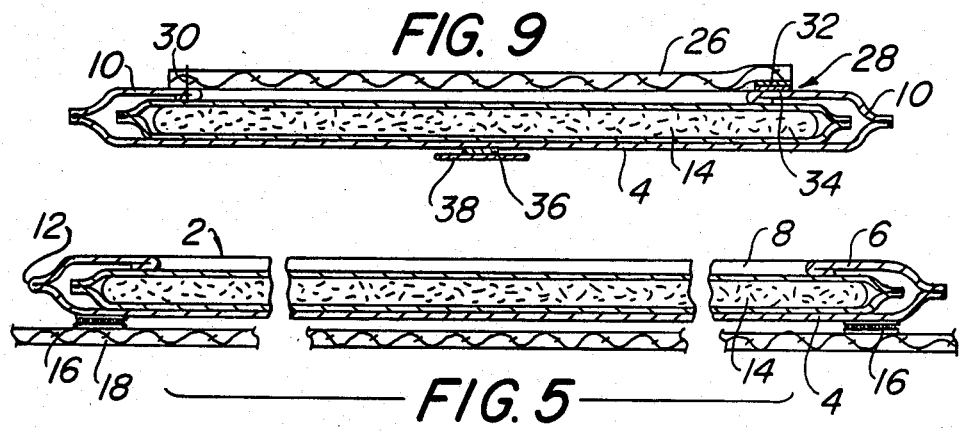
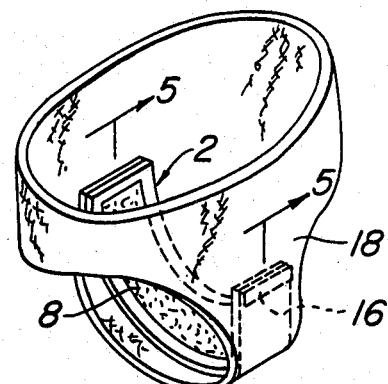

DISPOSABLE WATERPROOF ENCASEMENT AND PANTY FOR SANITARY PAD

This application is a continuation-in-part of my co-pending application Ser. No. 579,340, filed Feb. 13, 1984 now abandoned.

BACKGROUND

The present invention relates to a waterproof encasement for sanitary pads, and, more particularly, to a disposable encasement for temporarily converting the regular undergarment into a sanitary panty or stress incontinence garment. The invention further relates to such an encasement which is designed for the easy insertion and removal of the absorbent pad while securely retaining the pad within the encasement.

As used in this disclosure, sanitary pads and sanitary garments include absorbent pads and garments for use by men and women suffering from urinary incontinence and women during postpartum menstruation as well as women during monthly menstruation.

Numerous designs for waterproof encasements have been proposed such as disclosed in U.S. Pat. Nos. 4,352,356 to Tong, 4,044,769 to Papajohn, 2,977,957 to Clyne, and 2,985,170 to Title. However, one feature which all these prior art references have in common is that the encasement is formed as part of the sanitary garment. Therefore, women in particular, must have either two sets of undergarments, one for use during menstruation and one set to be used during other times, or must wear a regular set of undergarments over a sanitary napkin holder such as shown in Clyne, U.S. Pat. No. 2,977,957.

Newman, U.S. Pat. No. 2,551,691, discloses a sanitary napkin having a waterproof cover. The top portion of the cover has an opening to expose the sanitary napkin. However, the top and bottom halves of the waterproof covering are not secured together to form a waterproof fold. At each end of the covering there is an opening for passage of the sanitary napkin securing tabs. Furthermore, the napkin and covers are not designed to be secured to a regular undergarment but to be held in place by securing the tabs to clips on a sanitary belt.

In most of the piror art encasement designs, a major portion of the absorbent pad is covered by the waterproof front panel of the encasement. This was necessary to insure retention of the absorbent pad within the encasement.

One exception of this general design is the Tong urinary incontinence garment in which a pouch is formed by sewing a water penetrable panel to the crotch area of the garment. However, the only access to the absorbent pad is from one end of the panel and therefore it is difficult to insert a pad into the pouch and it is an unpleasent task to reach into the pouch to remove a urine-soaked pad.

Another exception is the disposable pad disclosed in Mammarella, U.S. Pat. No. 3,108,599, in which the pad is secured to the undergarment by four triangular pockets sewn to the crotch of the undergarment. The corners of the pad are inserted into the triangular pockets. However, the corners of the pad may easily slip out of the pockets. Further, the securing means is part of the undergarment and not part of an encasement as in the present invention. In fact the Mammarella pad does not include an encasement.

SUMMARY OF THE INVENTION

The present invention is directed to a disposable waterproof encasement for a sanitary pad which may be releasably secured to the crotch area of a regular undergarment. The present invention enables women to temporarily convert a regular undergarment into a sanitary panty thereby avoiding the necessity to purchase and use two different sets of undergarments.

By being releasably secured to the undergarment the encasement may be disposed with the used absorbent pad thereby avoiding direct contact with the urine-soaked used pad.

Another advantage of the invention is that the pad may be used a number of times and removed to facilitate cleaning of the encasement separately from the undergarment. Optionally, the encasement may be constructed of an inexpensive material so that it may be thrown away with the absorbent pad and a new encasement used with each replacement pad.

Further, the encasement is designed for easy insertion and removal of the absorbent pad while exposing a major portion of the pad and maintaining the pad securely within the encasement during use.

A principle object of the invention is to provide a waterproof encasement for a sanitary pad which securely maintains the sanitary pad at the desired location while being releasably secured to the undergarment for disposal of the encasement.

A further object of the invention is to provide an encasement which may be used with regular undergarments and has a waterproof margin around its entire periphery to deter soaking of the undergarment while exposing a major portion of the absorbent pad.

Another object is to provide an encasement which securely maintains the absorbent pad within the encasement while permitting easy insertion and removal of the pad.

An additional object is to provide an encasement which is simple and inexpensive construction.

The objects of the invention are met by an encasement having a waterproof back member and a waterproof marginal front member which are heat sealed to form a watertight fold around the entire periphery of the encasement. The marginal front portion forms an opening to expose an absorbent pad. In one embodiment, an adhesive strip is secured to the back panel of the encasement so that the encasement may be tacked to the crotch portion of everyday underwear to convert the underwear to a sanitary panty.

In another embodiment the encasement is secured to the pantry by three Velcro-type fasteners. The fasteners are secured to the encasement and panty ultrasonicly or with pressure-sensitive adhesive or solvent-activated adhesive.

In one embodiment the absorbent pad is adhesively secured to an elasticized rubber pad within the encasement. The elasticized rubber pad permits easy removal of the absorbent pad by controlling the amount of adhesion between the absorbent pad and the rubber pad.

To permit positive retention of the pad within the encasement while permitting easy insertion and removal, the encasement of another is constructed with an elongated strap, preferably of water-permeable material, bridging the central portion of the opening. One end portion of the strap is detachably securable to the marginal front portion by means of a Velcro-type material, for example. Other objects and advantages will appear hereinafter.

BRIEF DESCRIPTION OF THE DRAWINGS

For the purpose of illustrating the invention, there is provided in the drawings forms which are presently preferred, it being understood, however, that this invention is not limited to the precise arrangements and instrumentalities shown.

FIG. 4 is a top perspective showing the FIG. 1 embodiment secured to a regular undergarment.

FIG. 5 is a sectional view taken along line 5—5 in FIG. 4.

FIG. 6 is an enlarged plan view of the corner portion of a second embodiment of the present invention.

FIG. 7 is a perspective view of a third embodiment having elastic straps secured to opposite side portions of the encasement.

FIG. 9 is a sectional view taken along line 9—9 in FIG. 8.

DETAILED DESCRIPTION

One embodiment of the disposable encasement of the present invention is shown in FIGS. 1-5. The encasement 2 is formed by joining a back member 4 of waterproof material such as polypropylene or vinyl-coated nylon to a waterproof front member 6. The front member may be made with the same waterproof material as the back member. The front member is the same general shape as the back member and is joined at its outer margin to the outer margin of the back member. However, the front member consists essentially of a relatively narrow marginal band forming an opening 8 over the major area of the front member 6.

Figure 3:
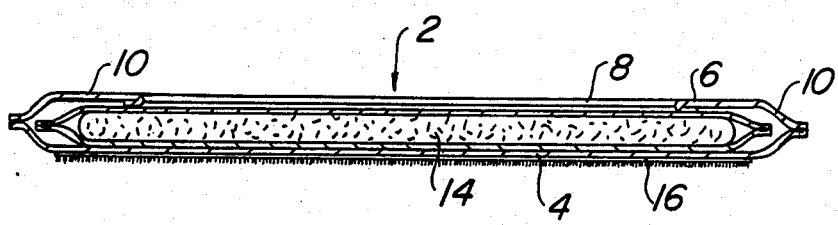
FIG. 3 is a sectional view taken along line 3—3 in FIG. 2.

As best shown in FIGS. 3 and 5, the encasement may be formed from one sheet by folding the back member 4 over the front member 6 at 12 and heat sealing the back member and front member together around the entire periphery. It is essential that the entire joint between the front and back members be liquid impermeable to prevent leakage of fluid from the absorbent pad to the clothing worn by the person using the encasement. Therefore it is preferred that the joints be heat sealed or have some other waterproofing means applied to the joints if the members are joined by stitching, for example.

An absorbent pad 14 may be inserted through the opening 8 and the edge portions of the absorbent pad tucked under the marginal edge portions of the front member. The width of the marginal front portion is sufficiently wide and the width and length of the absorbent pad sufficiently large that the marginal edge portions will overlap the edge portion of the absorbent pad and retain the pad within the encasement.

Although the shape of the disposable encasement is not to be limited, it is preferred that it be generally elongated. In the embodiment shown in the drawings, the encasement 2 and opening 8 are generally rectangular in outline. However, the encasement and/or opening may be generally oval or some other shape such as opening 8' in FIG. 10.

The encasement may be five and one half to twenty inches long and one and a half to seven inches wide. The opening may be approximately four to eighteen and one half inches by three quarters of an inch to five and one half inches. In the embodiment shown in FIG. 10, the opening may be about two inches to about six inches. An encasement having such dimensions will hold an absorbent pad of sufficient size to retain the discharge of a man or woman suffering from incontinence and yet not be so large as to be uncomfortable or unsightly.

Preferably the disposable encasement may be detatchably secured to the everyday undergarments of the user. By making the encasement releasably securable to everyday undergarments, the user need not purchase special and more expensive sanitary and incontinence undergarments. This is particularly desirable for women who need temporary protection during the menstrual cycle. By enabling the everyday garments to be converted into a sanitary garment, it is not necessary to have two sets of undergarments to be worn during the month.

It is desirable to design undergarments for use by persons suffering stress incontinence with a wider crotch than normal panties. This permits the use of a somewhat larger absorbent pad and encasement which is necessary in the stress incontinence undergarment.

One preferred means to releasably secure the encasement to the crotch area of an undergarment is the use of a Velcro-type material which is secured to the back member 4 of the encasement 2. As shown in FIGS. 1-5, a strip 16 of the hook-type Velcro fastener may be secured to the back member along both end portions. The encasement may be easily attached to an undergarment 18 as shown in FIGS. 4 and 5.

Another form of attachment means is shown in FIG. 6. A tab member 20 having the hook-type fastener material 22 secured to its underside may be attached to each corner of the encasement. The tab may be sewn or otherwise secured to the encasement.

A different embodiment for securing the encasement in place is shown in FIG. 7. In this embodiment, a pair of elastic strips 24 are secured to the opposed sides of the encasement to form resilient loops through which the legs of a user may be inserted and the elastic straps pulled up and around the hips to maintain the encasement and absorbent pad adjacent to the crotch of the wearer. The resilient loops may be releasably secured to the encasement by using a pressure sensitive or solvent activated adhesive, or by Velcro-type fasteners.

Figure 1:
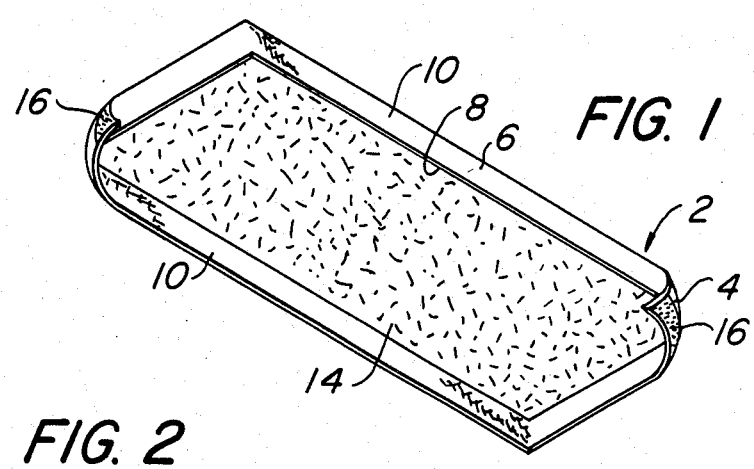
FIG. 1 is a top perspective view of an encasement and absorbent pad of the present invention with two corners folded upward to expose the back of the encasement.
Figure 2:
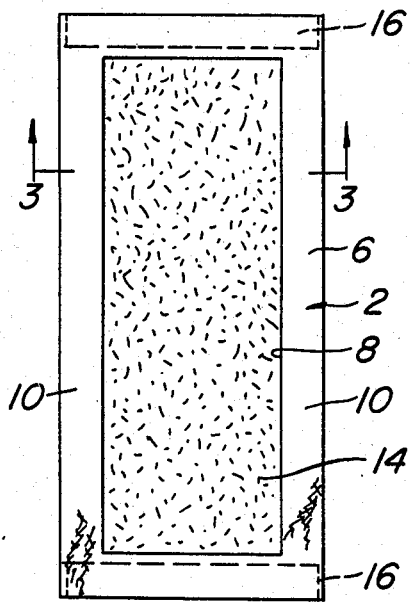
FIG. 2 is a plan view of the FIG. 1 embodiment.
Figure 8:
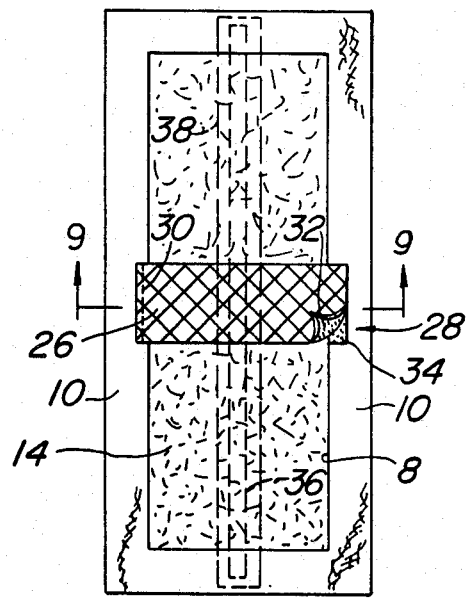
FIG. 8 is a plan view of a fourth embodiment having an elongated central strap.

Another means of detachably securing the encasement to an undergarment is a strip of adhesive applied to the back member 4 of the encasement. As shown in FIG. 8 and 9, the strip of releasable adhesive 36 may be applied to the longitudinal central portion of the back member 4. As shown in FIG. 9, the adhesive may be protected with a cover 38 such as a wax-coated strip of paper until the encasement is to be secured to the undergarment. Then the cover 38 is removed and the encasement is applied to the crotch area of the undergarment.

Figure 14:
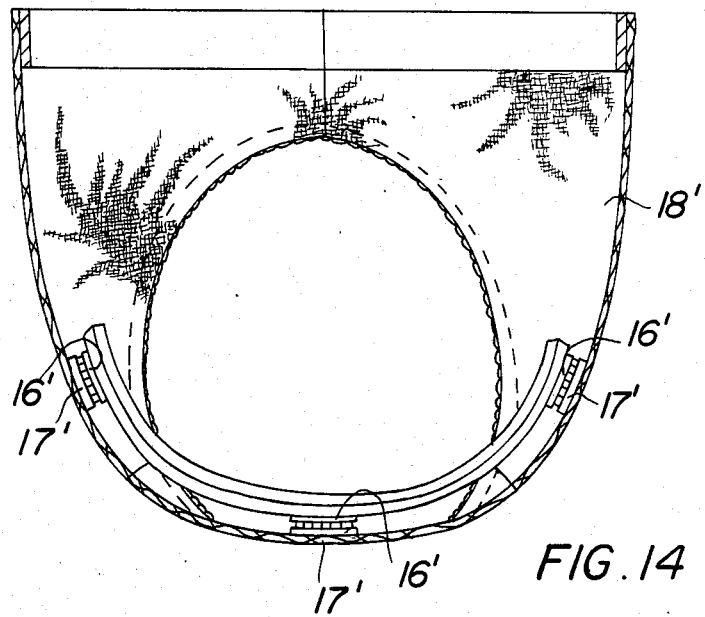
FIG. 14 is a sectional view taken along line 14—14 in FIG. 13.

The preferred means for releasably securing the encasement to an undergarment is shown in FIGS. 11 through 14. In this embodiment three strips of hook-type Velcro material 16' are secured to the back member 4'. Two of the strips are secured at either end of the encasement and the third strip is secured near the middle of the encasement. As best shown in FIG. 14, the hook type strips 16' are secured to corresponding loop type strips 17'.

Both the hook type and loop type strips may be secured to the encasement or undergarment with pressure sensitive adhesive or a solvent activated adhesive such as methyl ethyl ketone. Such strips, particularly the loop type strips 17' secured to the undergarment may be removed to convert the undergarment from a sanitary panty to a regular undergarment.

Preferably the Velcro-type strips are secured to the encasement and undergarment ultrasonicly. The three strips 16' may be secured to the encasement simultaneously by placing the encasement over a spring type anvil which opens the marginal front portions of the front member 6'. In like manner, the three loop type strips 17' may be simultaneously secured to the undergarment by placing the undergarment over an anvil and simultaneously applying ultrasonics to the undergarment around the periphery of the loop type strips 17'. The three strips 17' may be simultaneously secured to the undergarment using a single ultrasonic horn.

By securing the loop type strips to the undergarment, the encasement can be removed and the undergarment worn as a regular panty without discomfort. Persons with ultra-sensitive skin could turn the undergarment inside out to prevent contact of the loop type material with the body thereby permitting the undergarment to be worn as a regular panty without unsightly bulges.

A further advantage of making the encasement releasably securable to the undergarment is that it may be removed and separately washed in a stronger cleaning solution than would be desired to be used on a delicate panty. Also, by being able to wash the encasement separately, the panty will not come in contact with wash water containing urine or other discharge.

The sanitary napkins currently available are not fully encased with a waterproof member on the bottom and sides which may contact the undergarment. Therefore, there is always some risk that the absorbent pad will leak a portion of the discharge into the undergarment itself. The present invention overcomes this disadvantage.

To assist in retaining the absorbent pad 14 within the encasement while permiting easy insertion and removal of the absorbent pad, an elongated strap 26 may be secured to the longitudinal sides 10 of the front member, bridging the central portion of the opening 8. Preferably, the elongated strap is made from a water permeable material so that it will not interfere with absorption of discharge into the absorbent pad.

To make removal of the soaked absorbent easier and less unpleasent, it is preferred that one end portion of the elongated strap 26 be detachably securable to the marginal front portion of the encasement as shown in FIGS. 8 and 9 at 28. The opposite end portion 30 may be permanently secured to the marginal front portion of the encasement by stiching or an adhesive, for example. A strip 32 of hook-type material may be secured to the edge portion of the elongated strap 26 and a strip of loop-type material 34 may be secured to the front marginal portion of the encasement. While other forms of detatchable securable means such as a releasable adhesive may be used, the Velcro-type fastener is presently preferred.

Since the encasement is disposable as well as reusable, it may be part of a sanitary napkin kit which includes a supply of absorbent pads and at least one disposable waterproof encasement. The kit may include a sufficient supply of absorbent pads for one menstrual cycle and two or three encasements which may be used during a single cycle and then disposed.

Figure 10:
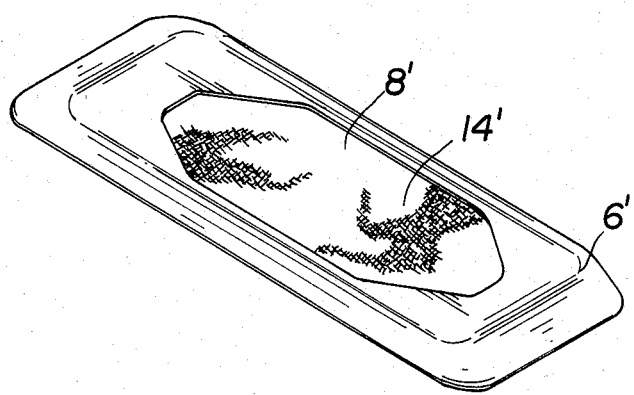
FIG. 10 is a top perspective view of a fifth embodiment.
Figure 11:
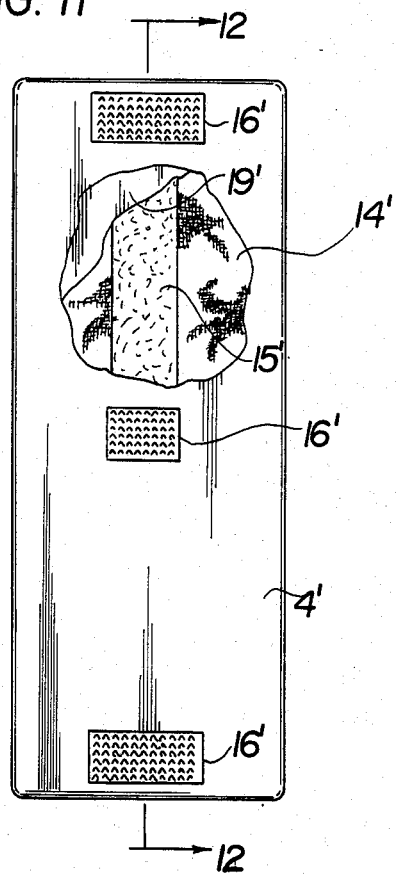
FIG. 11 is a bottom view of the FIG. 10 embodiment with parts broken away.
Figure 12:
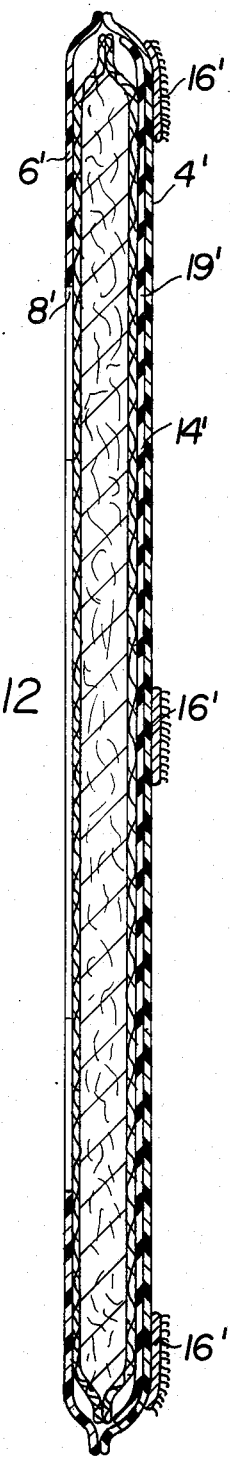
FIG. 12 is a sectional view taken along line 12—12 in FIG. 11.
Figure 13:
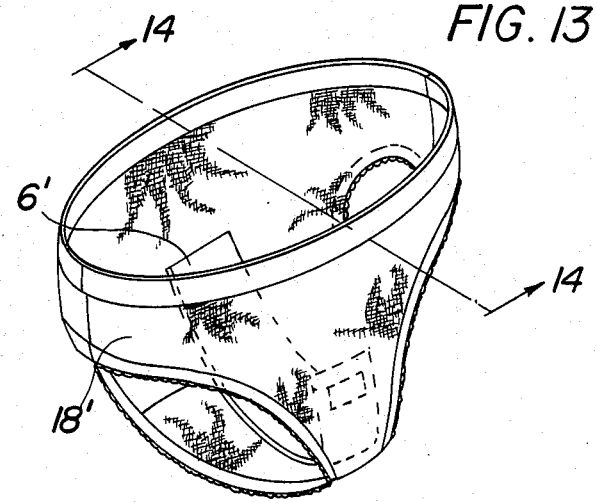
FIG. 13 is a top perspective showing the FIG. 10 embodiment secured to an undergarment.

To insure that the absorbent pad 14', shown in FIGS. 10 and 11, is retained within the encasement, frequently a strip of adhesive 15' is used to secure the absorbent pad to the encasement back member 4'. It has been found that the adhesive typically used adheres the absorbent pad to the encasement too tightly so that it becomes difficult to remove the used absorbent pad from the encasement. To overcome this problem, the surface of the back member within the encasement may be sprayed with a silicone spray; a lubricant such as silicone and mineral spirits may be applied to the back member; or a light dusting or powder may be applied to the back member. These methods all effectively reduce the adhesiveness of the absorbent pad adhesive strip 15'. However, it is preferred to insert a pad 19' between the absorbent pad 14' and the back member of the encasement.

The pad 19' may be the approximate size and shape of the back member. It should be larger than the opening 8' and preferred shape is an oval having a width and length greater than the opening 8'. The pad 19' may be made of an elasticized gum rubber, latex, or a polystretch material such as polyurethane or a polyvinyl.

It has been found that the pad or layer 19' not only reduces the adhesiveness of the absorbent pad adhesive strip 14' but also performs an important function during the manufacture of the encasement. The rubber layer 19' prevents sealing of the front member and back member together during the ultrasonic application of the hook type strips 16'.

The present invention may be embodied in other specific forms without departing from the spirit or essential attributes thereof and, accordingly, reference should be made to the appended claims, rather than to the foregoing specification, as indicating the scope of the invention.

What is claimed is:

1. A liquidproof encasement for an absorbent pad having an adhesive strip comprising a liquidproof back member, a liquidproof front member secured to the marginal portion of said back member to form a liquid-tight seam around the entire periphery of the encasement, said front member having an opening for an absorbent pad insertable, within said encasement, and means to reduce the adherence of said adhesive strip of such absorbent pad to the encasement comprising a layer of gum rubber between the front member and the back member having a size greater than the opening in the front member.

2. The liquidproof encasement according to claim 1, wherein the adherence reducing layer is gum rubber coated on at least one side with a powder.

3. A liquidproof encasement for an absorbent pad having an adhesive strip comprising a liquidproof back member, a liquidproof front member secured to the marginal portion of said back member to form a liquid-tight seam around the entire periphery of the encasement, said front member having an opening for an absorbent pad insertable, within said encasement, and means to reduce the adherence of said adhesive strip of such absorbent pad to the encasement comprising a lubricant applied to the back member.

4. The liquidproof encasement according to claim 3, wherein the lubricant is a silicone spray, a powder, or silcone and mineral spirits.

5. A sanitary napkin kit comprising a plurality of absorbent pads; at least one disposable liquidproof encasement for said pad, said encasement including a liquidproof back member and a liquidproof front member secured to the marginal portion of said back member to form a liquid-tight seam around the entire periphery of the encasement, said front member having an opening for the insertion of one of the absorbent pads within the encasement, said absorbent pads having a strip of adhesive to aid in maintaining the pad within the encasement; and means for reducing the adherence of said absorbent pad adhesive strip comprising a layer of gum rubber between the front member and the back member having a size greater than the opening of the front member.

6. The kit according to claim 5, wherein the gum rubber is coated on at least one side with a powder.

7. The kit according to claim 5, wherein the adherence reducing means is a lubricant applied to the back member.

8. The kit according to claim 7, wherein the lubricant is a silicone spray, a powder, or silicone and mineral spirits.

* * * * *